US012766319B2

(12) United States Patent
Wasserman et al.

(10) Patent No.: US 12,766,319 B2
(45) Date of Patent: Oct. 20, 2026

(54) DELIVERING TUMOR TREATING FIELDS (TTFields) USING IMPLANTED SHEETS OF GRAPHITE

(71) Applicant: Novocure GmbH, Root (CH)

(72) Inventors: Yoram Wasserman, Haifa (IL); Stas Obuchovsky, Haifa (IL); Nataliya Kuplennik, Kanata (CA); David Shapiro, Haifa (IL)

(73) Assignee: Novocure GmbH, Baar (CH)

( * ) Notice: Subject to any disclaimer, the term of this patent is extended or adjusted under 35 U.S.C. 154(b) by 469 days.

(21) Appl. No.: 18/129,510

(22) Filed: Mar. 31, 2023

(65) Prior Publication Data

US 2023/0310849 A1 Oct. 5, 2023

Related U.S. Application Data

(60) Provisional application No. 63/325,650, filed on Mar. 31, 2022.

(51) Int. Cl.
*A61N 1/36* (2006.01)

(52) U.S. Cl.
CPC ................................ *A61N 1/36002* (2017.08)

(58) Field of Classification Search
None
See application file for complete search history.

(56) References Cited

U.S. PATENT DOCUMENTS

| | | | | | |
|---|---|---|---|---|---|
| 4,033,357 | A * | 7/1977 | Helland | ................. | A61N 1/056 607/121 |
| 6,868,289 | B2 | 3/2005 | Palti | | |
| 7,016,725 | B2 | 3/2006 | Palti | | |
| 7,089,054 | B2 | 8/2006 | Palti | | |
| 7,136,699 | B2 | 11/2006 | Palti | | |
| 7,333,852 | B2 | 2/2008 | Palti | | |
| 7,467,011 | B2 | 12/2008 | Palti | | |
| 7,519,420 | B2 | 4/2009 | Palti | | |

(Continued)

FOREIGN PATENT DOCUMENTS

| | | | |
|---|---|---|---|
| CN | 113769267 | A | 12/2021 |
| CN | 113926079 | A | 1/2022 |

(Continued)

OTHER PUBLICATIONS

International Search Report and Written Opinion issued in application No. PCT/IB2023/053279 dated Jul. 11, 2023.

(Continued)

*Primary Examiner* — Michael W Kahelin
(74) *Attorney, Agent, or Firm* — Potomac Law Group, PLLC

(57) ABSTRACT

Alternating electric fields (e.g., tumor treating fields, a.k.a. TTFields) may be applied to a target region in a subject's body via sheets of graphite that are implanted in the subject's body. One or more ports configured for affixation to the subject's body include or connect to one or more mating electrical connectors. Electrical conductors are positioned to route electrical signals between the electrical connector(s) and the sheets of graphite. The alternating electric fields are applied to the target region by applying (via the ports) an alternating voltage between two sheets of graphite that are positioned on opposite sides of the target region.

17 Claims, 6 Drawing Sheets

(56) References Cited

U.S. PATENT DOCUMENTS

| | | | | |
|---|---|---|---|---|
| 7,565,205 | B2 | 7/2009 | Palti | |
| 7,565,206 | B2 | 7/2009 | Palti | |
| 7,599,745 | B2 | 10/2009 | Palti | |
| 7,599,746 | B2 | 10/2009 | Palti | |
| 7,706,890 | B2 | 4/2010 | Palti | |
| 7,715,921 | B2 | 5/2010 | Palti | |
| 7,805,201 | B2 | 9/2010 | Palti | |
| 7,890,183 | B2 | 2/2011 | Palti et al. | |
| 7,912,540 | B2 | 3/2011 | Palti | |
| 7,917,227 | B2 | 3/2011 | Palti | |
| 8,019,414 | B2 | 9/2011 | Palti | |
| 8,027,738 | B2 | 9/2011 | Palti | |
| 8,170,684 | B2 | 5/2012 | Palti | |
| 8,175,698 | B2 | 5/2012 | Palti et al. | |
| 8,229,555 | B2 | 7/2012 | Palti | |
| RE43,618 | E | 8/2012 | Palti | |
| 8,244,345 | B2 | 8/2012 | Palti | |
| 8,406,870 | B2 | 3/2013 | Palti | |
| 8,447,395 | B2 | 5/2013 | Palti et al. | |
| 8,447,396 | B2 | 5/2013 | Palti et al. | |
| 8,465,533 | B2 | 6/2013 | Palti | |
| 8,706,261 | B2 | 4/2014 | Palti | |
| 8,715,203 | B2 | 5/2014 | Palti | |
| 8,718,756 | B2 | 5/2014 | Palti | |
| 8,764,675 | B2 | 7/2014 | Palti | |
| 9,023,090 | B2 | 5/2015 | Palti | |
| 9,023,091 | B2 | 5/2015 | Palti | |
| 9,039,674 | B2 | 5/2015 | Palti et al. | |
| 9,056,203 | B2 | 6/2015 | Palti et al. | |
| 9,440,068 | B2 | 9/2016 | Palti et al. | |
| 9,655,669 | B2 | 5/2017 | Palti et al. | |
| 9,750,934 | B2 | 9/2017 | Palti et al. | |
| 9,910,453 | B2 | 3/2018 | Wasserman et al. | |
| 10,188,851 | B2 | 1/2019 | Wenger et al. | |
| 10,441,776 | B2 | 10/2019 | Kirson et al. | |
| 10,779,875 | B2 | 9/2020 | Palti et al. | |
| 10,967,167 | B2 | 4/2021 | Hagemann et al. | |
| 11,103,698 | B2 | 8/2021 | Chang et al. | |
| 11,191,956 | B2 | 12/2021 | Giladi et al. | |
| 2004/0176804 | A1 | 9/2004 | Palti | |
| 2005/0209642 | A1 | 9/2005 | Palti | |
| 2005/0222623 | A1* | 10/2005 | Kroll | A61N 1/326 607/2 |
| 2006/0167499 | A1 | 7/2006 | Palti | |
| 2006/0276858 | A1 | 12/2006 | Palti | |
| 2007/0225766 | A1* | 9/2007 | Palti | A61N 1/40 607/2 |
| 2007/0239213 | A1 | 10/2007 | Palti | |
| 2009/0076366 | A1 | 3/2009 | Palti | |
| 2010/0331811 | A1* | 12/2010 | Imran | A61N 1/0436 604/501 |
| 2012/0029419 | A1 | 2/2012 | Palti | |
| 2012/0283726 | A1 | 11/2012 | Palti | |
| 2013/0197608 | A1* | 8/2013 | Eiger | A61N 1/37 607/2 |
| 2014/0330268 | A1 | 11/2014 | Palti et al. | |
| 2016/0324435 | A1* | 11/2016 | Kuzum | A61N 1/0551 |
| 2017/0042614 | A1* | 2/2017 | Salahieh | A61B 1/00082 |
| 2017/0120041 | A1 | 5/2017 | Wenger et al. | |
| 2017/0215939 | A1 | 8/2017 | Palti et al. | |
| 2017/0281934 | A1 | 10/2017 | Giladi et al. | |
| 2018/0001075 | A1 | 1/2018 | Kirson et al. | |
| 2018/0008708 | A1 | 1/2018 | Giladi et al. | |
| 2018/0050200 | A1 | 2/2018 | Wasserman et al. | |
| 2018/0160933 | A1 | 6/2018 | Urman et al. | |
| 2018/0202991 | A1 | 7/2018 | Giladi et al. | |
| 2018/0280687 | A1 | 10/2018 | Carter et al. | |
| 2019/0117956 | A1 | 4/2019 | Wenger et al. | |
| 2019/0117963 | A1 | 4/2019 | Travers et al. | |
| 2019/0117970 | A1 | 4/2019 | Schmidt et al. | |
| 2019/0224474 | A1 | 7/2019 | Yang et al. | |
| 2019/0308016 | A1 | 10/2019 | Wenger et al. | |
| 2020/0001069 | A1 | 1/2020 | Kirson et al. | |
| 2020/0009376 | A1 | 1/2020 | Chang et al. | |
| 2020/0009377 | A1 | 1/2020 | Chang et al. | |
| 2020/0016067 | A1 | 1/2020 | Gotlib et al. | |
| 2020/0023179 | A1 | 1/2020 | Bomzon et al. | |
| 2020/0061360 | A1 | 2/2020 | Hagemann et al. | |
| 2020/0061361 | A1 | 2/2020 | Hagemann et al. | |
| 2020/0069937 | A1 | 3/2020 | Naveh et al. | |
| 2020/0078582 | A1 | 3/2020 | Alon et al. | |
| 2020/0108031 | A1 | 4/2020 | Borst et al. | |
| 2020/0114141 | A1 | 4/2020 | Bomzon et al. | |
| 2020/0114142 | A1 | 4/2020 | Bomzon et al. | |
| 2020/0121728 | A1 | 4/2020 | Wardak et al. | |
| 2020/0129761 | A1 | 4/2020 | Bomzon et al. | |
| 2020/0146586 | A1 | 5/2020 | Naveh et al. | |
| 2020/0155835 | A1 | 5/2020 | Wasserman et al. | |
| 2020/0171297 | A1 | 6/2020 | Kirson et al. | |
| 2020/0179512 | A1 | 6/2020 | Giladi et al. | |
| 2020/0219261 | A1 | 7/2020 | Shamir et al. | |
| 2020/0269037 | A1 | 8/2020 | Hagemann et al. | |
| 2020/0269041 | A1 | 8/2020 | Zeevi et al. | |
| 2020/0269042 | A1 | 8/2020 | Giladi et al. | |
| 2020/0330756 | A1* | 10/2020 | Schmidt | A61N 1/36002 |
| 2020/0368525 | A1 | 11/2020 | Maag et al. | |
| 2021/0031031 | A1 | 2/2021 | Wasserman et al. | |
| 2021/0038584 | A1 | 2/2021 | Voloshin-Sela | |
| 2021/0060334 | A1 | 3/2021 | Avraham et al. | |
| 2021/0069503 | A1 | 3/2021 | Tran et al. | |
| 2021/0138233 | A1 | 5/2021 | Deslauriers | |
| 2021/0162228 | A1 | 6/2021 | Urman et al. | |
| 2021/0177492 | A1 | 6/2021 | Travers et al. | |
| 2021/0187277 | A1 | 6/2021 | Wasserman et al. | |
| 2021/0196348 | A1 | 7/2021 | Wasserman | |
| 2021/0199640 | A1 | 7/2021 | Patel et al. | |
| 2021/0203250 | A1 | 7/2021 | Wasserman | |
| 2021/0268247 | A1 | 9/2021 | Story et al. | |
| 2021/0290944 | A1* | 9/2021 | Hong | A61N 1/32 |
| 2021/0299440 | A1 | 9/2021 | Deslauriers et al. | |
| 2021/0308446 | A1 | 10/2021 | Alon et al. | |
| 2021/0330950 | A1 | 10/2021 | Hagemann et al. | |
| 2021/0346694 | A1 | 11/2021 | Wasserman et al. | |
| 2021/0379362 | A1 | 12/2021 | Smith et al. | |
| 2021/0408383 | A1 | 12/2021 | Kalra et al. | |
| 2022/0095997 | A1 | 3/2022 | Wasserman | |
| 2022/0096821 | A1 | 3/2022 | Kirson et al. | |
| 2022/0118249 | A1 | 4/2022 | Bomzon et al. | |
| 2022/0161028 | A1 | 5/2022 | Giladi et al. | |
| 2022/0193435 | A1 | 6/2022 | Wasserman et al. | |
| 2022/0267445 | A1 | 8/2022 | Tran et al. | |
| 2022/0280787 | A1 | 9/2022 | Bomzon et al. | |
| 2022/0288395 | A1 | 9/2022 | Voloshin-Sela et al. | |
| 2022/0313992 | A1 | 10/2022 | Wasserman | |
| 2022/0323753 | A1 | 10/2022 | Voloshin-Sela et al. | |
| 2022/0387784 | A1 | 12/2022 | Kirson et al. | |
| 2022/0395699 | A1 | 12/2022 | Doyle | |
| 2022/0409893 | A1 | 12/2022 | Wasserman et al. | |
| 2023/0000384 | A1 | 1/2023 | Wasserman et al. | |
| 2023/0001197 | A1 | 1/2023 | Wasserman et al. | |
| 2023/0001221 | A1 | 1/2023 | Farber | |
| 2023/0009366 | A1 | 1/2023 | Voloshin-Sela et al. | |
| 2023/0019638 | A1 | 1/2023 | Wasserman | |
| 2023/0037806 | A1 | 2/2023 | Wasserman et al. | |
| 2023/0043071 | A1 | 2/2023 | Wasserman et al. | |
| 2023/0098801 | A1 | 3/2023 | Carlson | |
| 2023/0141087 | A1 | 5/2023 | Giladi et al. | |
| 2023/0168242 | A1 | 6/2023 | Sarkisian et al. | |
| 2023/0188055 | A1 | 6/2023 | Wasserman | |
| 2023/0191123 | A1 | 6/2023 | Wasserman et al. | |
| 2023/0201616 | A1 | 6/2023 | Carlson | |
| 2023/0218912 | A1 | 7/2023 | Giladi et al. | |

FOREIGN PATENT DOCUMENTS

| | | | |
|---|---|---|---|
| KR | 20160134469 | A | 11/2016 |
| KR | 20200016102 | A | 2/2020 |

OTHER PUBLICATIONS

Kim et al., "Stretchable and Transparent Biointerface Using Cell-Sheet-Graphene Hybrid for Electrophysiology and Therapy of Skel-

(56) References Cited

OTHER PUBLICATIONS etal Muscle," Advanced Functional Materials, vol. 25, pp. 3207-3217, Mar. 2016.

* cited by examiner

DELIVERING TUMOR TREATING FIELDS (TTFields) USING IMPLANTED SHEETS OF GRAPHITE

CROSS REFERENCE TO RELATED APPLICATIONS

This application claims the benefit of U.S. Provisional Application 63/325,650, filed Mar. 31, 2022, which is incorporated herein by reference in its entirety.

BACKGROUND

TTFields (Tumor Treating Fields) therapy is a proven approach for treating tumors using alternating electric fields at frequencies between 50 kHz-1 MHz, such as from 100 kHz-500 kHz. In the prior art Optune® system for delivering TTFields, the TTFields are delivered to patients via four transducer arrays placed on the patient's skin in close proximity to a tumor. The transducer arrays are arranged in two pairs. One of those pairs is positioned on the left and right sides of the target region (e.g., a glioblastoma); and the other one of those pairs is positioned on the front and back of the target region. Each transducer array is connected via a cable to an AC voltage generator. The AC voltage generator (a) sends an AC current through one pair of arrays during a first period of time; then (b) sends an AC current through the other pair of arrays during a second period of time; then repeats steps (a) and (b) for the duration of the treatment.

SUMMARY OF THE INVENTION

One aspect of this application is directed to a first apparatus for applying an alternating electric field to a target region in a subject's body. The first apparatus comprises a sheet of graphite, a port, and an electrical conductor. The sheet of graphite has a front face and a rear face. The port is configured for affixation to a living subject's body, and the port has an outer surface that includes or connects to a mating electrical connector. The electrical conductor is positioned to route an electrical signal between the electrical connector and the sheet of graphite.

In some embodiments of the first apparatus, the sheet of graphite is positioned subcutaneously or implanted within the subject's body, with the front face of the sheet of graphite facing the target region. And the mating electrical connector is positioned to be accessible from outside the subject's body. Some embodiments of the first apparatus further comprise an AC signal generator configured to supply an AC voltage. In some embodiments of the first apparatus, the sheet of graphite is a mesh sheet.

Some embodiments of the first apparatus further comprise a layer of a biocompatible insulating polymer material disposed on at least one of the faces of the sheet of graphite, wherein the insulating polymer material has a dielectric constant of at least 10.

Some embodiments of the first apparatus further comprise a sheet of biocompatible material configured to support the rear face of the sheet of graphite. In some embodiments, the sheet of biocompatible material configured to support the rear face of the sheet of graphite may be, or may comprise, a sheet of graphite mesh. Some embodiments of the first apparatus further comprise a sheet of biocompatible graphite mesh configured to support the rear face of the sheet of graphite.

In some embodiments of the first apparatus, the sheet of graphite comprises pyrolytic graphite, graphitized polymer film, or graphite foil made from compressed high purity exfoliated mineral graphite, or at least partially oxidized forms thereof. In some embodiments of the first apparatus, the electrical conductor comprises a wire made of graphite. In some embodiments of the first apparatus, the sheet of graphite comprises a synthetic graphite.

Another aspect of this application is directed to a second apparatus for applying an alternating electric field to a target region in a subject's body. The second apparatus comprises a sheet of graphite having a front face and a rear face, and a layer of a biocompatible insulating polymer material disposed on at least one of the faces of the sheet of graphite. The sheet of graphite is configured for implantation into a living subject's body. The insulating polymer material has a dielectric constant of at least 10.

In some embodiments of the second apparatus, the sheet of graphite is positioned subcutaneously or implanted within the subject's body, with the front face of the sheet of graphite facing the target region. In some embodiments of the second apparatus, the sheet of graphite is a mesh sheet.

Some embodiments of the second apparatus further comprise a sheet of biocompatible material configured to support the rear face of the sheet of graphite. In some embodiments, the sheet of biocompatible material configured to support the rear face of the sheet of graphite may be, or may comprise, a sheet of graphite mesh. Some embodiments of the second apparatus further comprise a sheet of biocompatible graphite mesh configured to support the rear face of the sheet of graphite.

Some embodiments of the second apparatus further comprise a biocompatible electrically conductive wire positioned to route an electrical signal to the sheet of graphite. In some embodiments of the second apparatus, the wire is made of graphite.

In some embodiments of the second apparatus, the sheet of graphite comprises pyrolytic graphite, graphitized polymer film, or graphite foil made from compressed high purity exfoliated mineral graphite, or at least partially oxidized forms thereof. In some embodiments of the second apparatus, the sheet of graphite comprises a synthetic graphite.

Another aspect of this application is directed to a first method of applying an alternating electric field to a target region in a subject's body. The first method comprises applying an alternating voltage between a first sheet of graphite that has been previously implanted in the subject's body and a second sheet of graphite that has been previously implanted in the subject's body. The first sheet of graphite and the second sheet of graphite are positioned on opposite sides of the target region.

Some instances of the first method further comprise implanting the first sheet of graphite in the subject's body prior to the applying; and implanting the second sheet of graphite in the subject's body prior to the applying.

In some instances of the first method, a layer of a biocompatible insulating polymer material having a dielectric constant of at least 10 is disposed on at least one face of the first sheet of graphite, and a layer of a biocompatible insulating polymer material having a dielectric constant of at least 10 is disposed on at least one face of the second sheet of graphite.

In some instances of the first method, the first sheet of graphite is supported by a first sheet of biocompatible material, and the second sheet of graphite is supported by a second sheet of biocompatible material. In some embodiments, the first sheet of biocompatible material is a sheet of graphite mesh.

In some instances of the first method, the first sheet of graphite comprises pyrolytic graphite, graphitized polymer film, or graphite foil made from compressed high purity exfoliated mineral graphite, or at least partially oxidized forms thereof. In some instances of the first method, the first sheet of graphite comprises a synthetic graphite,

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1A:
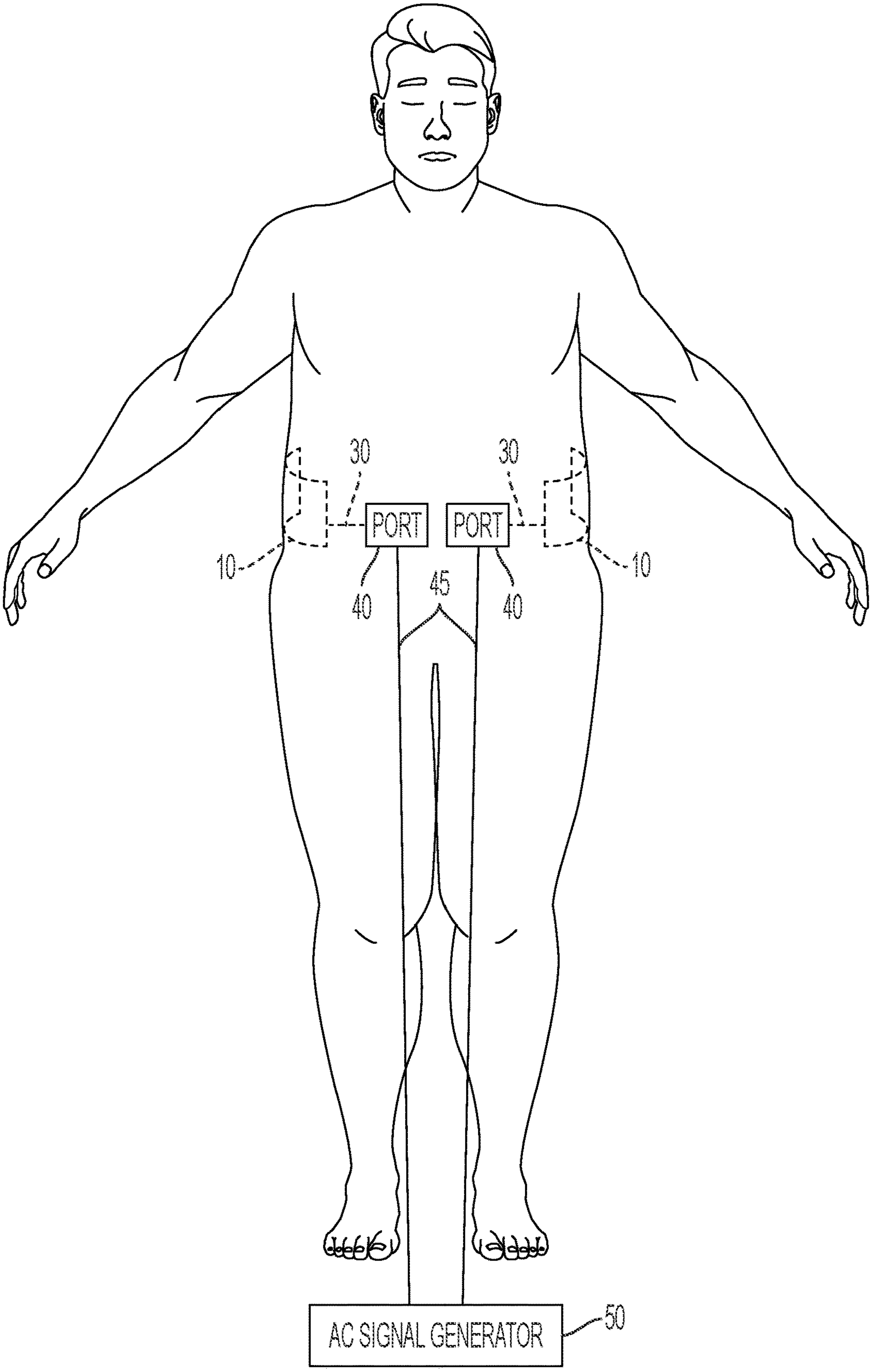
FIG. 1A depicts two sheets of graphite that are implanted in a subject's body on opposite sides of a target region.

Instead of using transducer arrays positioned on the patient's skin to deliver TTFields, the embodiments described herein use electrodes that are implanted within a patient's body to deliver TTFields. Implanting the electrodes can provide a number of potential advantages. These potential advantages include (1) hiding of the arrays from people with whom the patient interacts; (2) improving patient comfort (by avoiding the skin irritation, sensations of heating, and/or limitations on motion that can result from arrays that are positioned on the patient's skin); (3) improving electrical contact between the electrodes and the patient's body; (4) eliminating the need for shaving regions on which the arrays are placed (as hair growth can interfere with the delivery of TTFields); (5) avoiding the risk that detachment of the electrodes will interrupt the delivery of TTFields; (6) significantly reducing the power required to deliver TTFields (e.g., by reducing the physical distance between the electrodes and the tumor and bypassing anatomical structures that have high resistivity, e.g., the skull); (7) significantly reducing the weight of the device that must be carried by the patient (e.g., by using smaller batteries to take advantage of the reduced power requirements); (8) avoiding the skin irritation that can occur when transducer arrays are positioned on the patient's skin; and (9) making it possible to deliver TTFields to anatomic structures that cannot be treated using transducer arrays positioned on the patient's skin (e.g., the spinal cord, which is surrounded by highly conductive cerebrospinal fluid that is in turn surrounded by the bony structure of the spine, both of which interfere with the penetration of TTFields into the spinal cord itself).

Improvements are sought over the prior art implantable medical devices for delivering alternating electric fields to a target region within a subject's body. Such devices have been bulky due to the number of electrodes required in an array and the size of the electrode elements in the array. Moreover, the operating currents have been low (typically below 1 A) because of the need to avoid hot spots that could damage the tissue in the body, and the low operating current has limited their efficacy. The present application addresses these and other important issues.

Preferably, each of the electrodes that is implanted within a patient's body is formed using a sheet of graphite. Using graphite sheets provides significant advantages with respect to other materials because graphite sheets spread the electrical current (which arrives from the AC signal generator) out in directions that are parallel to the front face of the sheet, and also spread the heat out in directions that are parallel to the front face of the sheet. These two advantages are significant when the graphite sheet is a sheet of high purity exfoliated mineral graphite. And these two advantages can be even more significant when the graphite sheet is a sheet of synthetic graphite, such as a sheet of pyrolytic graphite, or graphitized polymer film (e.g., graphitized polyimide). Because the current and heat in these embodiments are both spread out over a larger area of the front face of each electrode, hot spots are eliminated (or at least minimized). Accordingly, the surface area of the electrodes can be reduced without generating excessive heat and hot spots which would necessitate operating at a lower current; and/or the current can be increased (with respect to embodiments that do not include a graphite sheet). And this increase in current will advantageously increase the efficacy of the TTFields treatment. Moreover, graphite is biocompatible.

FIG. 1A depicts two sheets of graphite 10 that are implanted in a subject's body on opposite sides of a target region located within the subject's body. Each sheet of graphite has a corresponding port 40, and a wire 30 or another electrical conductor routes an electrical signal between each port 40 and the respective sheet of graphite 10. The ports 40 are designed to facilitate safe attachment and detachment of the distal end of a cable 45 from outside the body. This may be accomplished, for example, by incorporating a connector into each of the ports 40, as described below in connection with FIG. 2. The proximal ends of both cables 45 terminate at an AC signal generator 50. As a result, when the AC signal generator 50 imposes an AC signal between the two cables 45, a corresponding voltage will appear between the two implanted sheets of graphite 10.

Figure 1B:
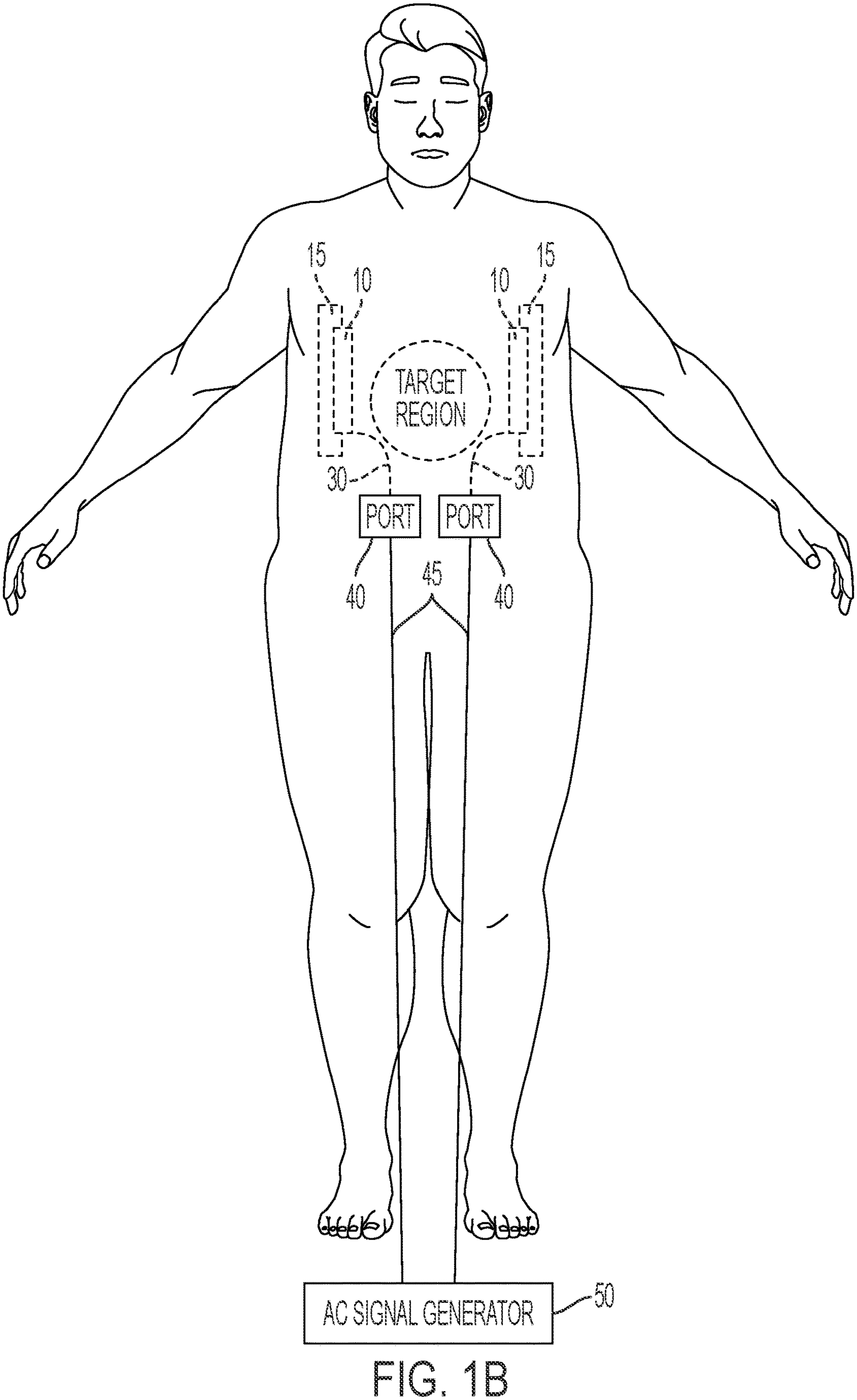
FIG. 1B depicts a variation of the FIG. 1A embodiment that includes an additional layer of material.

FIG. 1A shows the graphite sheets implanted subcutaneously adjacent to the subject's skin. However, in other embodiments, the graphite sheets may be implanted further into the subject's body. For example, the graphite sheets may be located adjacent to, and on either side of, a target (such as a tumor) in a target region or in a target location, or may be adjacent to, or wrapped around, an organ of the body within which the target is located (e.g., as depicted in FIG. 1B). The graphite sheets may be supported on a substrate or by a backing layer. FIG. 1B depicts graphite sheets implanted further into the subject's body and incorporating a sheet of biocompatible material 15 positioned behind the rear face of the sheet of graphite 10, and this sheet 15 is configured to support the rear face of the sheet of graphite 10. Suitable materials for the sheet 15 include, for example, biocompatible polymers, ceramics, composites, metals, etc. (e.g., acrylic polymers, titanium metal). Alternatively, the sheet of biocompatible material 15 may be a sheet of graphite mesh.

Optionally, additional sheets of graphite (not shown) may be implanted in the subject's body. For example, in addition to the pair of implanted sheets of graphite 10 on the right and left sides of the subject's abdomen illustrated in FIG. 1, an additional pair of graphite sheets may be implanted on the front and back of the subject's abdomen. When additional sheets of graphite are provided, signals from the AC signal generator 50 are provided to those graphite sheets at appropriate times. Further optionally, a third pair of graphite sheets may be implanted in like manner. Again, additional implanted graphite sheets may be implanted subcutaneously adjacent to the subject's skin, or may be implanted further into the subject's body.

In further embodiments, one or more electrodes may be implanted within the body, and one or more electrodes may be positioned outside the body. For example, one (or more) pair of electrodes may be implanted in the body, while one (or more) pair of electrodes may be positioned outside the body. Alternatively, one electrode of a pair of electrodes may be implanted in the body, while the other of that pair of electrodes may be positioned outside the body; etc. It is to be understood that, throughout this disclosure, these options are included even though not specifically recited. That is, reference to two electrodes or two sheets of graphite implanted in the subject's body or positioned subcutaneously within the subject's body refers also to at least one electrode or sheet of graphite implanted in the subject's body or positioned subcutaneously within the subject's body and one or more electrodes or sheets of graphite positioned externally on the subject's body or clothing. In each case, the sheets of graphite are positioned so that the front face of each sheet of graphite faces the target region in the subject's body.

The location at which the sheets of graphite 10 are installed will depend on the position of the tumor that is being treated. Examples of appropriate locations include subcutaneous locations just below the surface of the subject's skin, between the subject's skin and skull, or just beneath the subject's skull. Other appropriate locations include positioning one or more sheets of graphite 10 deeper within a subject's brain (e.g., in a resection cavity that has been formed during surgery), or positioning one or more sheets of graphite within the subject's torso, such as within the abdomen (e.g., on either side of an organ such as the pancreas).

The sheet of graphite 10 could be made of pyrolytic graphite, graphitized polymer film, graphite foil made from compressed high purity exfoliated mineral graphite, or other forms of graphite. The sheet of graphite has anisotropic properties with respect to both electrical conductivity properties and thermal conductivity properties, such that the sheet spreads out both the heat and the current more evenly over a larger surface area.

The anisotropic thermal properties include directional thermal properties. Specifically, the sheet has a first thermal conductivity in a direction that is perpendicular to its front face. And the thermal conductivity of the sheet in directions parallel to the front face is more than two times higher than the first thermal conductivity. In some preferred embodiments, the thermal conductivity in the parallel directions is more than ten times higher than the first thermal conductivity. For example, the thermal conductivity of the sheet in directions that are parallel to the front face may be more than: 1.5 times, 2 times, 3 times, 5 times, 10 times, 20 times, 100 times, 200 times, or even more than 1,000 times higher than the first thermal conductivity.

The anisotropic electrical properties include directional electrical properties. Specifically, the sheet has a first resistance in a direction that is perpendicular to its front face. And the resistance of the sheet in directions parallel to the front face is less than the first resistance. In some preferred embodiments, the resistance in the parallel directions is less than half of the first resistance or less than 10% of the first resistance. For example, the resistance of the sheet 10 in directions that are parallel to the front face may be less than: 75%, 50%, 40%, 30%, 20%, 10%, 5%, 1%, 0.5%, or even less than 0.1% of the first resistance.

For example, the thermal conductivity of a sheet of pyrolytic graphite in directions that are in the x-y plane is between 10 times and 20 times higher than its thermal conductivity in the perpendicular z-direction; and the electrical resistivity of a sheet of pyrolytic graphite in directions that are in the x-y plane is approximately three orders of magnitude (1,000 times) lower than its electrical resistivity in the perpendicular z-direction.

Examples of suitable forms of graphite include synthetic graphite, such as pyrolytic graphite (including, but not limited to, Pyrolytic Graphite Sheet (PGS), available from Panasonic Industry, Kadoma, Osaka, Japan), or graphitized polymer film, e.g., graphitized polyimide film, (including, but not limited to, that supplied by Kaneka Corp., Moka, Tochigi, Japan. Graphite foil made from compressed high purity exfoliated mineral graphite may also be suitable (for example, but not limited to, that supplied by MinGraph® 2010A Flexible Graphite, available from Mineral Seal Corp., Tucson, Arizona, USA). In alternative embodiments, conductive anisotropic materials other than graphite may be used instead of graphite.

Figure 2:
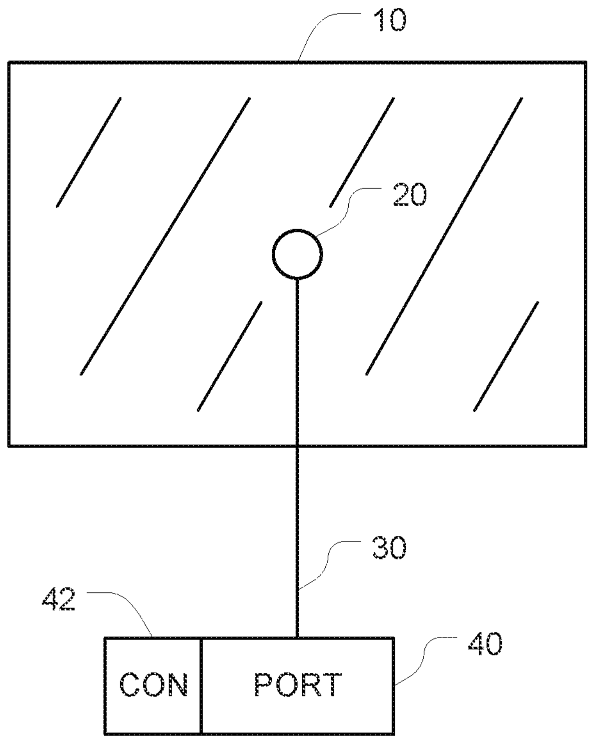
FIG. 2 depicts a plan view of an apparatus for applying an alternating electric field to the target region in a subject's body.

FIG. 2 depicts an apparatus for applying an alternating electric field to a target region in a subject's body. This apparatus includes a sheet of graphite 10 that has a front face and a rear face. The sheet of graphite 10 could be, for example, a non-porous, continuous sheet with no openings or pores that pass therethrough, or a continuous sheet with openings or pores that pass therethrough. The sheet of graphite 10 may be flexible to facilitate implantation, and may be implanted into the subject's body using techniques that are similar to the techniques for implanting hernia meshes into a subject's body, including but not limited to laparoscopic techniques. When flexible sheets of graphite are used, they can be inserted into the subject's body through a small incision in a folded or rolled-up state. The sheet of graphite 10 is then subsequently unfolded or unrolled at the desired location within the subject's body to make a larger surface area available. The flexibility of the graphite sheet helps to minimize the size of the surgical incision and procedure.

A port 40 is configured for affixation to a living subject's body. The port(s) may be located directly adjacent to the implanted sheets of graphite, in near proximity to the implanted sheets of graphite, or may traverse the skin at a location some distance from the implanted sheets of graphite. The port has an outer surface that includes or connects to a mating electrical connector 42. The affixation of the port 40 to the subject's body may be implemented by implanting the port such that the connecter 42 remains accessible from the outside. The connector 42 is configured to accept the cable 45 (shown in FIGS. 1A and 1B). Preferably, the connector 42 is configured so that the cable 45 can be disconnected, e.g., when the subject does not want to be encumbered by those cables.

Figure 3:
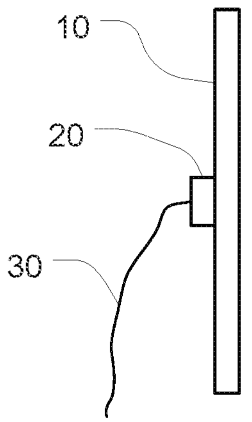
FIG. 3 is a side view of the FIG. 2 apparatus.

One or more electrical conductors are positioned to route an electrical signal between the electrical connector 42 and the sheet of graphite. In the embodiment illustrated in FIG. 2, these conductors are implemented using a terminal 20 (e.g., a conductive metal) that is attached to the sheet of graphite 10, a wire 30, and portions of the port 40. A side view of portions of this embodiment are shown in FIG. 3. The wire 30 in these embodiments could be, for example, a biocompatible metal wire or a graphite wire. And the terminal 20 in these embodiments could be connected to the sheet of graphite 10 using, for example, a conductive adhesive. In alternative embodiments, the wire 30 can be omitted, in which case the port 40 would be connected directly to the sheet of graphite 10 using, for example, a suitable conductive adhesive. In these latter examples, the conductive portions of the port 40 and the conductive adhesive serve as the electrical conductors.

Referring now to FIGS. 1A-3, the sheets of graphite 10 are positioned subcutaneously or implanted within the subject's body, with the front face of the sheet of graphite facing the target region. The mating electrical connector 42 is positioned to be accessible from outside the subject's body. When the cables 45 are attached to the ports 40 via the electrical connector 42, the respective sheet of graphite 10 can be energized by the AC signal generator 50 via the respective cables 45, ports 40, and wire/conductor 30. When an AC voltage is applied between the two sheets of graphite 10, an electric field will be conductively coupled into the region that lies between those two sheets of graphite (which includes the target region in the subject's body).

Figure 4:
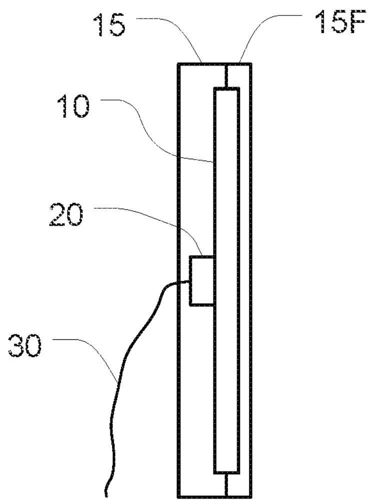
FIG. 4 depicts a variation of the FIG. 2-3 embodiment that includes two additional layers of material.

In some embodiments, a layer of a biocompatible insulating polymer material 15F may be disposed on the front face of the sheet of graphite 10, as shown in FIG. 4. The insulating polymer material has a dielectric constant of at least 10 (or, in some embodiments, at least 20).

Suitable materials for use as the insulating polymer material 15F include poly(vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CtFE)" and "Poly(VDF-TrFE-CFE)", respectively. Optionally, ceramic nanoparticles may be mixed into the Poly (VDF-TrFE-CtFE) and/or Poly(VDF-TrFE-CFE) to form a "nanocomposite." Optionally, these ceramic nanoparticles may comprise ferroelectric metal oxides (e.g., barium titanate and/or barium strontium titanate). In alternative embodiments, a different polymer that provides a high dielectric constant (e.g., at least 10 or at least 20) may be used. Examples of alternative polymeric materials that may be used in place of Poly(VDF-TrFE-CtFE) and/or Poly(VDF-TrFE-CFE) include the following: (1) ceramic nanoparticles mixed into at least one of Poly(VDF-TrFE), P(VDF-HFP), PVDF, or other polymers (where HFP is hexafluoropropylene); and (2) barium titanate and/or barium strontium titanate ceramic nanoparticles mixed into at least one of Poly (VDF-TrFE), P(VDF-HFP), PVDF. In other embodiments, the insulating polymer material 15F is formed by mixing ceramic nanoparticles into at least one other polymer.

In some embodiments, including the embodiment depicted in FIG. 4, a sheet of biocompatible material 15 is positioned behind the rear face of the sheet of graphite 10, and this sheet 15 is configured to support the rear face of the sheet of graphite 10. Suitable materials for the sheet 15 include, for example, biocompatible polymers, ceramics, composites, metals, etc. (e.g., acrylic polymers, titanium metal). Alternatively, the sheet of biocompatible material 15 may be a sheet of graphite mesh. Optionally, the sheet of biocompatible material may also be included in other embodiments herein, such as, for example, the embodiment shown in FIG. 3, configured to support the rear face of the sheet of graphite.

Figure 5:
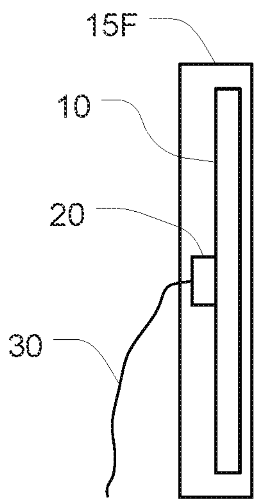
FIG. 5 depicts another variation of the FIG. 2-3 embodiment that includes additional layers of material.

In some embodiments, the biocompatible insulating polymer material 15F is disposed on both faces of the sheet of graphite 10, as shown in FIG. 5. The insulating polymer material has a dielectric constant of at least 10 (or, in some embodiments, at least 20), and may be made from the same materials as the layer 15F described above in connection with FIG. 4.

To use the embodiments described above in connection with FIG. 4-5, two sheets of graphite 10 are positioned subcutaneously or implanted within the subject's body, with the front face of each sheet of graphite facing the target region. When an AC voltage is applied between the two sheets of graphite 10, an electric field will be capacitively coupled (due to the polymer layer 15F) into the region that lies between those two sheets of graphite (which includes the target region in the subject's body).

Figure 6:
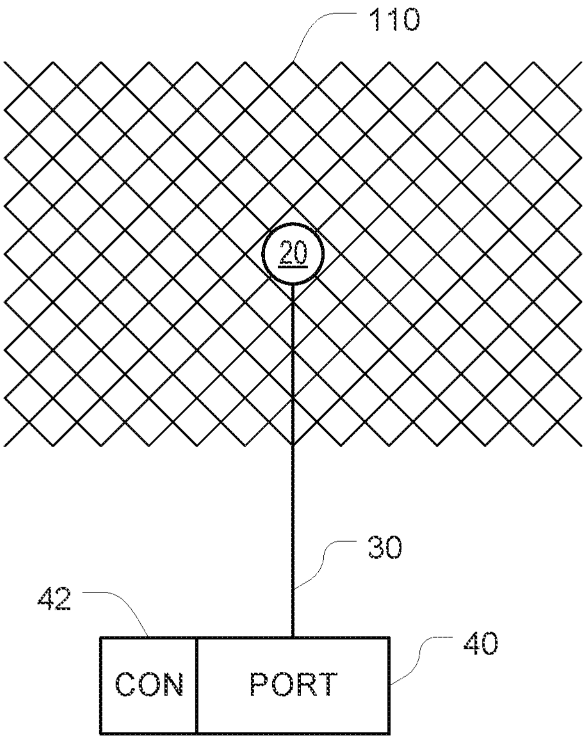
FIGS. 6 and 7 are plan and side views of another apparatus for applying an alternating electric field to a target region in a subject's body.
Figure 7:
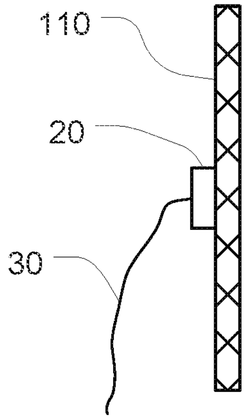

FIGS. 6 and 7 are plan and side views of another apparatus for applying an alternating electric field to a target region in a subject's body. This apparatus is similar to the embodiment described above in connection with FIGS. 2 and 3, except that in place of the sheets of graphite described above in connection with FIGS. 2 and 3, the sheet of graphite is a sheet-shaped piece of graphite mesh 110. The sheet of graphite mesh 110 may be flexible to facilitate implantation, and may be implanted into the subject's body using techniques that are similar to the techniques for implanting hernia meshes into a subject's body (e.g., as described above in connection with FIG. 2). The sheet of graphite mesh 110 could be made of pyrolytic graphite, graphitized polymer film, graphite foil made from compressed high purity exfoliated mineral graphite, or other forms of graphite.

To use the FIG. 6-7 embodiments, two sheets of graphite mesh 110 are positioned subcutaneously or implanted within the subject's body, with the front face of each sheet of graphite facing the target region. When an AC voltage is applied between the two sheets of graphite mesh 110, an electric field will be conductively coupled into the region that lies between those two sheets of graphite mesh (which includes the target region in the subject's body). Variations of the embodiments of FIGS. 4 and 5 may be applicable for the embodiments of FIGS. 6 and 7.

Figure 8:
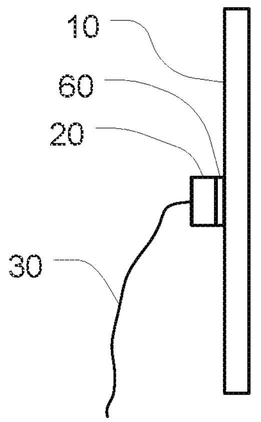
FIG. 8 is a side view of another apparatus for applying an alternating electric field to a target region in a subject's body.

FIG. 8 is a side view of another apparatus for applying an alternating electric field to a target region in a subject's body. This apparatus is similar to the embodiment described above in connection with FIGS. 2 and 3, except that an additional layer of material 60 with a high dielectric constant (e.g., at least 10 or at least 20) is positioned between the terminal 20 and the sheet of graphite 10. When this embodiment is used for implantation into a subject's body, and an AC voltage is applied between two sheets of graphite 10 implanted in the body, an electric field will be capacitively coupled into the region that lies between those two sheets of graphite 10, which includes the target region in the subject's body. The layer of material 60 may be formed from high dielectric constant ceramic materials or from the same high dielectric constant polymeric materials as the layer 15F described above in connection with FIG. 4. Keeping the layer of material 60 with the high dielectric constant thin (e.g., less than 20 μm, less than 10 μm, or less than 5 μm) is preferable in order to improve the capacitive coupling. Variations of the embodiments of FIGS. 4 and 5 or FIGS. 6 and 7 may be applicable for the FIG. 8 embodiment.

Figure 9:
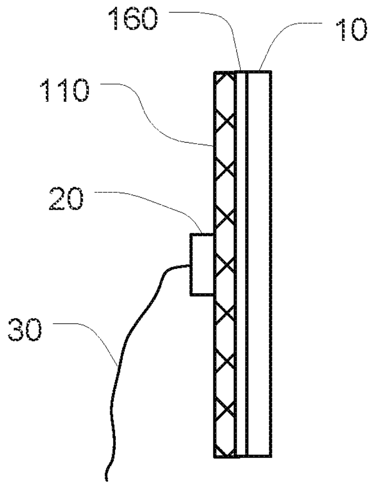
FIG. 9 is a side view of another apparatus for applying an alternating electric field to a target region in a subject's body.

FIG. 9 is a side view of another apparatus for applying an alternating electric field to a target region in a subject's body. This apparatus is similar to the embodiment described above in connection with FIGS. 2 and 3, except that two additional layers are included. More specifically, a layer of graphite mesh 110 is positioned behind the sheet of graphite 10, and an additional layer of material 160 with a high dielectric constant (e.g., at least 10 or at least 20) is positioned between the layer of graphite mesh 110 and the sheet of graphite 10. When this embodiment is positioned subcutaneously or implanted within the subject's body, and an AC voltage is applied between two sheets of graphite 10 implanted in the body, an electric field will be capacitively coupled into the region that lies between those two sheets of graphite 10, which includes the target region in the subject's body. The layer of material 160 may be formed from high dielectric constant ceramic materials or from the same high dielectric constant polymeric materials as the layer 15F described above in connection with FIG. 4, and the layer 160 is preferably thin (e.g., less than 20 μm, less than 10 μm, or less than 5 μm).

In other embodiments, layers 110 and 160 in FIG. 9 may be reversed and the resulting apparatus may operate similarly. In other embodiments, the layer of graphite mesh 110 may be replaced with a second sheet of graphite 10 such that the layer of material 160 with a high dielectric constant (e.g., at least 10 or at least 20) is positioned between two sheets of graphite 10, and the resulting apparatus may operate similarly.

Figure 10:
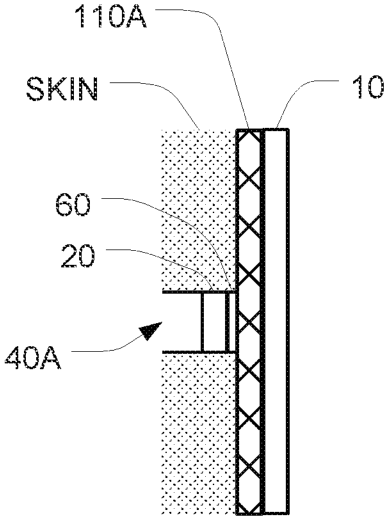
FIG. 10 is a side view of another apparatus for applying an alternating electric field to a target region in a subject's body.

FIG. 10 is a side view of another apparatus for applying an alternating electric field to a target region in a subject's body. This apparatus is similar to the embodiment described above in connection with FIGS. 2 and 3, except that instead of connecting the sheet of graphite 10 to the port (e.g., port 40 in FIGS. 1A, 1B, 2, and 6) via a wire 30, the sheet of graphite 10 and a port 40A are combined into an integrated unit that is implanted into the subject's body just beneath the subject's skin. The electrical connection to the sheet of graphite 10 is made via this port 40A.

In the embodiment illustrated in FIG. 10, a support layer made from graphite mesh 110A is positioned behind the sheet of graphite 10. But in alternative embodiments, this support layer could be made from a different material (e.g., an acrylic polymer) or omitted entirely.

In the embodiment illustrated in FIG. 10, a layer of material 60 with a high dielectric constant (e.g., at least 10 or at least 20) is interposed between the electrical terminal 20 and the sheet of graphite 10. When this layer of material 60 is included, and an AC voltage is applied between two implanted sheets of graphite 10 (e.g., via two ports 40A), an electric field will be capacitively coupled into the region that lies between those two sheets of graphite 10, which includes the target region in the subject's body. The layer of material 60 may be formed from high dielectric constant ceramic materials or from the same high dielectric constant polymeric materials as the layer 15F described above in connection with FIG. 4, and the layer 60 is preferably thin (e.g., less than 20 μm, less than 10 μm, or less than 5 μm).

In alternative embodiments, the layer of material 60 can be omitted, in which case the terminal 20 of the port 40A makes electrical contact with the sheet of graphite 10, either directly, or via optional support layer 110A. In these alternative embodiments, when an AC voltage is applied between the two sheets of graphite 10 (e.g., via two ports 40A), an electric field will be conductively coupled into the region that lies between those two sheets of graphite 10, which includes the target region in the subject's body. Optionally, electrical contact may be enhanced between terminal 20 of the port 40A and the sheet of graphite 10, or the support layer 110A, by using a connecting layer of a conductive adhesive.

FIG. 10 illustrates one electrode assembly situated directly adjacent to the port 40A. However, other layered constructs of the electrode assembly described herein may also be used in this manner and, indeed, situating the electrode assembly directly adjacent to the port 40A may be preferable for the embodiments incorporating the high dielectric material layer (e.g., 15F in FIGS. 4 and 5; 60 in FIG. 8; and 160 in FIG. 9).

Figure 11:
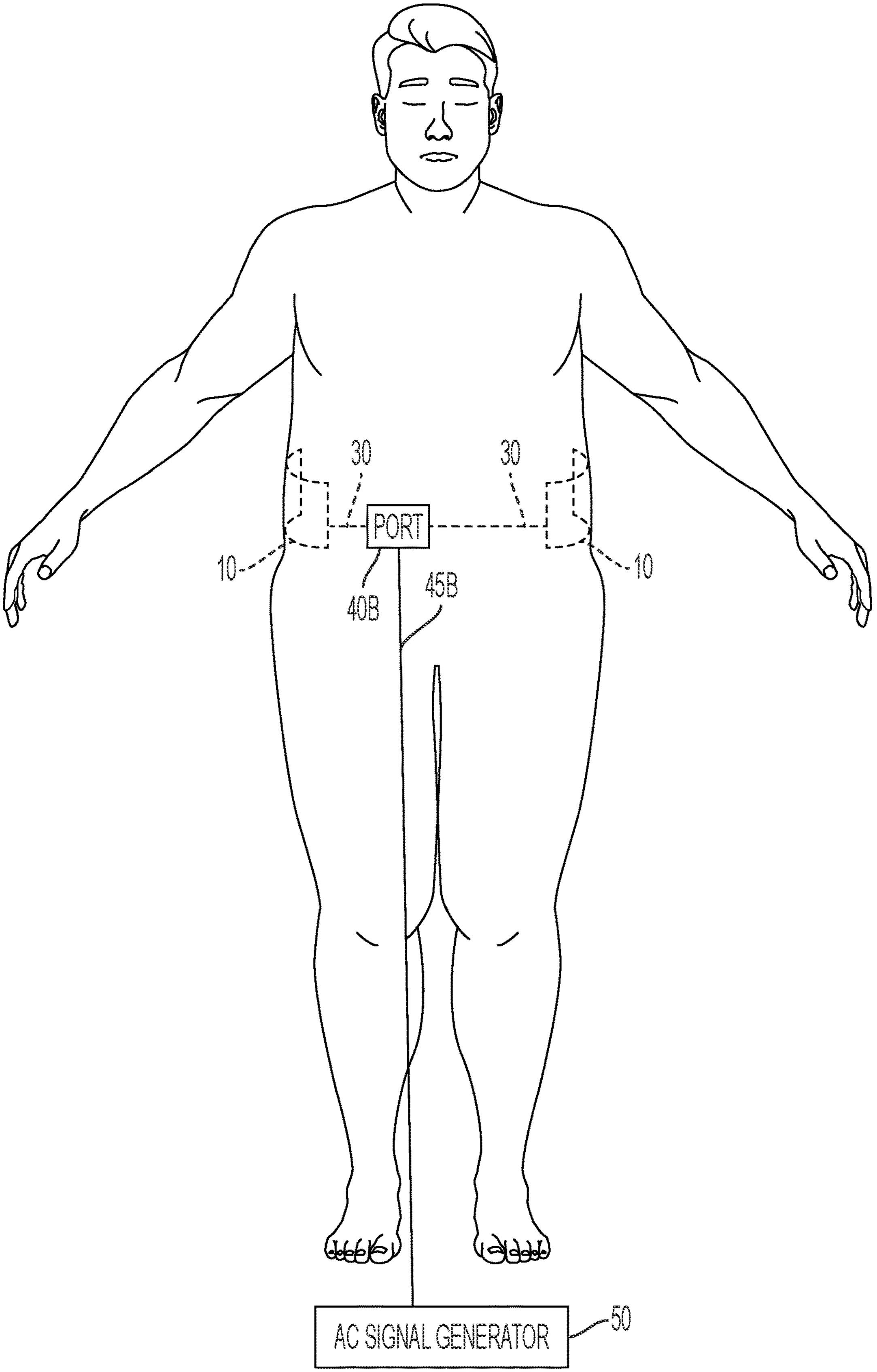
FIG. 11 depicts a variation of the FIG. 1A embodiment that utilizes a single multi-conductor port.

FIG. 11 depicts another approach for connecting the implanted graphite sheets that is similar to the approach depicted in the embodiments of FIGS. 1A and 1B, except that instead of providing a separate port 40 for connecting with each sheet of graphite, respectively, this FIG. 11 approach utilizes a single multi-conductor port 40B that accepts a multi-conductor cable 45B from the AC signal generator 50. An individual wire 30 or other electrical conductor runs through the subject's body to route one of the electrical signals that arrives via the multi-conductor cable 45B between the single port 40B and one sheet of graphite 10. And a second wire 30 (or other electrical conductor) runs through the subject's body to route the other electrical signal that arrives via the multi-conductor cable 45B between the single port 40B and the other sheet of graphite 10. In this FIG. 11 embodiment, the construction of the sheet of graphite 10 and the connections thereto (e.g., using the wires 30) may be as described above in connection with FIGS. 2-9. When more than two sheets of graphite are implanted into the subject's body, the single port 45B can direct signals to all of the implanted sheets 10 (e.g., using an individual wire 30 for each implanted sheet of graphite).

The hardware described above in connection with FIG. 1-11 may be used to practice the following method of applying an alternating electric field to a target region in a subject's body. The method comprises applying an alternating voltage between a first sheet of graphite 10 that has been previously implanted in the subject's body and a second sheet of graphite 10 that has been previously implanted in the subject's body, wherein the first sheet of graphite and the second sheet of graphite are positioned on opposite sides of the target region. In some embodiments, the frequency of the alternating voltage is between 50 kHz and 1 MHz, or between 100 kHz and 500 kHz.

At some point in time prior to the applying, the first and second sheets of graphite 10 are implanted in the subject's body.

Optionally, a layer of a biocompatible insulating polymer material 15F having a dielectric constant of at least 10 is disposed on at least one face of the first sheet of graphite 10, and a layer of a biocompatible insulating polymer material 15F having a dielectric constant of at least 10 is disposed on at least one face of the second sheet of graphite 10.

Optionally, the first sheet of graphite 10 is supported by a first sheet of biocompatible material 15, and the second sheet of graphite is supported by a second sheet of biocompatible material 15. In each case, the biocompatible support may be a sheet of graphite mesh.

The sheets of graphite 10 may be made of a synthetic graphite. The sheets of graphite 10 may be made of pyrolytic graphite, graphitized polymer film, or graphite foil made from compressed high purity exfoliated mineral graphite. In some embodiments, the sheets of graphite 10 may be oxidized (or partially oxidized) sheets of graphite, or the sheets may be constructed of oxidized (or partially oxidized) graphite, which may be used to improve adhesion to the sheets of graphite. As described above in connection with FIG. 6-7, the first sheet of graphite could be a mesh sheet 110.

In any of the embodiments and methods described herein, sensors for measuring temperature (such as thermistors) may be positioned on or near the graphite sheets 10 so that tissue temperature can be controlled and thermal damage to tissue avoided.

In any of the embodiments and methods described herein, adhesion between components or layers of the electrode assembly, or between the electrode assembly and the surrounding tissues, can be achieved using a conductive adhesive.

In any of the embodiments and methods described herein, it is preferred to connect internal wiring/circuitry to external wiring/circuitry outside of the body via one or more ports positioned on or across the subject's skin, as indicated in FIGS. 1A, 1B and 11. However, in alternative embodiments, the one or more ports are not present and a separate connection is utilized outside the body (for example, one or more connectors). The use of a port has the advantage of allowing the subject to disconnect the external wiring at a connector at the port, thereby allowing the subject to be unencumbered of external wiring at chosen times.

In any of the embodiments and methods described herein, it is preferred to locate the electric field generator and/or AC signal generator outside of the body, as indicated in FIGS. 1A, 1B and 11, which also show a wired connection with components inside the body. However, in alternative embodiments, the external device may communicate wirelessly with components that are inside the body. It is desirable to minimize the number of transcutaneous wires. For example, a small electronics package may be implanted in the body, connected by a single wire (for example, the same wire that supplies the electric field) to the external unit and electronics. The implanted electronics package may include circuitry and switches that can be controlled wirelessly from outside the body.

The implanted electrodes of the embodiments described herein advantageously may be significantly smaller than prior art implantable electrodes. In some embodiments, the surface area of the sheets of graphite (and also the front face of the electrode assembly) may be from approximately 1-40 $cm^2$ or greater, and the electrode assembly may have a thickness of less than 1 mm, or may be greater than 1 mm.

Optionally, in addition to implanting two sheets of graphite on opposite sides of a target region as described above, and subsequently applying an AC voltage between those two sheets of graphite in order to induce an alternating electric field in the target region, an additional two sheets of graphite may be implanted in the subject's body on opposite sides of the target region. For example, if the original two sheets of graphite are implanted on the left and right sides of a target region, the additional two sheets of graphite should be implanted in front of and in back of the target region. When an additional two sheets of graphite are implanted, applying an AC voltage between the original two sheets of graphite will impose an alternating electric field with a first orientation in the target region, and applying an AC voltage between the additional two sheets of graphite will impose an alternating electric field with a second orientation in the target region. Details of construction of the additional sheets of graphite, as well as structures for supporting those sheets, are as described above in connection with FIGS. 2-10.

In alternative embodiments, instead of implanting two sheets of graphite on opposite sides of a target region, and applying an AC voltage between those two sheets of graphite in order to induce an alternating electric field in the target region (as described above), only a single sheet of graphite can be implanted on one side of the target region. In these embodiments, a second electrode (which may or may not be constructed using graphite) is positioned outside the subject's body on the opposite side of the target region, and an AC voltage is applied between the implanted sheet of graphite and the second electrode (i.e., the external electrode).

In these embodiments, an alternating electric field is applied to a target region in a subject's body by applying an alternating voltage between a sheet of graphite that has been previously implanted in the subject's body and a second electrode that is positioned outside the subject's body. Details of the construction of the implanted sheet of graphite (as well as structures for supporting the sheet of graphite) are as described above in connection with FIGS. 2-10. The sheet of graphite and the second electrode are positioned on opposite sides of the target region. Prior to applying the alternating voltage, the first sheet of graphite is implanted in the subject's body, and the second electrode is positioned in contact with the subject's body.

Embodiments illustrated under any heading or in any portion of the disclosure may be combined with embodiments illustrated under the same or any other heading or other portion of the disclosure unless otherwise indicated herein or otherwise clearly contradicted by context.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of applying an alternating electric field to a target region in a subject's body, the method comprising:

applying an alternating voltage between a first sheet of graphite that has been previously implanted in the subject's body and a second sheet of graphite that has been previously implanted in the subject's body, wherein the first sheet of graphite and the second sheet of graphite are positioned on opposite sides of the target region, and wherein the first sheet of graphite has a first resistance in a direction that is perpendicular to its front face and the resistance of the sheet in directions parallel to the front face is less than half of the first resistance.

2. The method of claim 1, further comprising:

implanting the first sheet of graphite in the subject's body prior to the applying; and implanting the second sheet of graphite in the subject's body prior to the applying.

3. The method of claim 1, wherein a layer of a biocompatible insulating polymer material having a dielectric constant of at least 10 is disposed on at least one face of the first sheet of graphite, and wherein a layer of a biocompatible insulating polymer material having a dielectric constant of at least 10 is disposed on at least one face of the second sheet of graphite.

4. The method of claim 1, wherein the first sheet of graphite is supported by a first sheet of biocompatible material, and wherein the second sheet of graphite is supported by a second sheet of biocompatible material.

5. The method of claim 1, wherein the first sheet of graphite is a mesh sheet.

6. The method of claim 1, wherein the first sheet of graphite comprises pyrolytic graphite, graphitized polymer film, or graphite foil made from compressed high purity exfoliated mineral graphite, or at least partially oxidized forms thereof.

7. The method of claim 1, wherein the first sheet of graphite comprises pyrolytic graphite.

8. The method of claim 1, wherein the first sheet of graphite has an area of at least 1 $cm^2$.

9. The method of claim 1, wherein the first sheet of graphite has an area of 1-40 $cm^2$.

10. The method of claim 1, wherein the first sheet of graphite has a first thermal conductivity in a direction that is perpendicular to its front face and the thermal conductivity of the sheet in directions parallel to the front face is more than two times higher than the first thermal conductivity.

11. The method of claim 1, wherein internal wiring/circuitry in the subject's body is connected to external wiring/circuitry outside of the subject's body via one or more ports positioned on or across the subject's skin.

12. The method of claim 1, wherein internal wiring/circuitry in the subject's body is connected to external wiring/circuitry outside of the subject's body via one or more separate connector positioned outside the subject's body.

13. The method of claim 1, wherein the method further comprises implanting an additional two sheets of graphite in the subject's body on opposite sides of the target region, and applying an AC voltage between the original two sheets of graphite to impose an alternating electric field with a first orientation in the target region, and applying an AC voltage between the additional two sheets of graphite to impose an alternating electric field with a second orientation in the target region.

14. The method of claim 1, wherein the alternating voltage is supplied by an electric field generator and/or AC signal generator that is located outside of the subject's body.

15. The method of claim 1, wherein the alternating voltage has a frequency between 50 kHz and 1 MHz.

16. The method of claim 1, wherein the alternating voltage has a frequency between 100 kHz and 500 kHz.

17. A method of applying an alternating electric field to a target region in a subject's body, the method comprising:

applying an alternating voltage between a first sheet of graphite that has been previously implanted in the subject's body and a second sheet of graphite that has been previously implanted in the subject's body, wherein the first sheet of graphite and the second sheet of graphite are positioned on opposite sides of the target region, and wherein the first sheet of graphite is supported by a first sheet of biocompatible material, wherein the second sheet of graphite is supported by a second sheet of biocompatible material, and wherein the first sheet of biocompatible material or the second sheet of biocompatible material comprises a sheet of graphite mesh.

* * * * *